Figure 1:
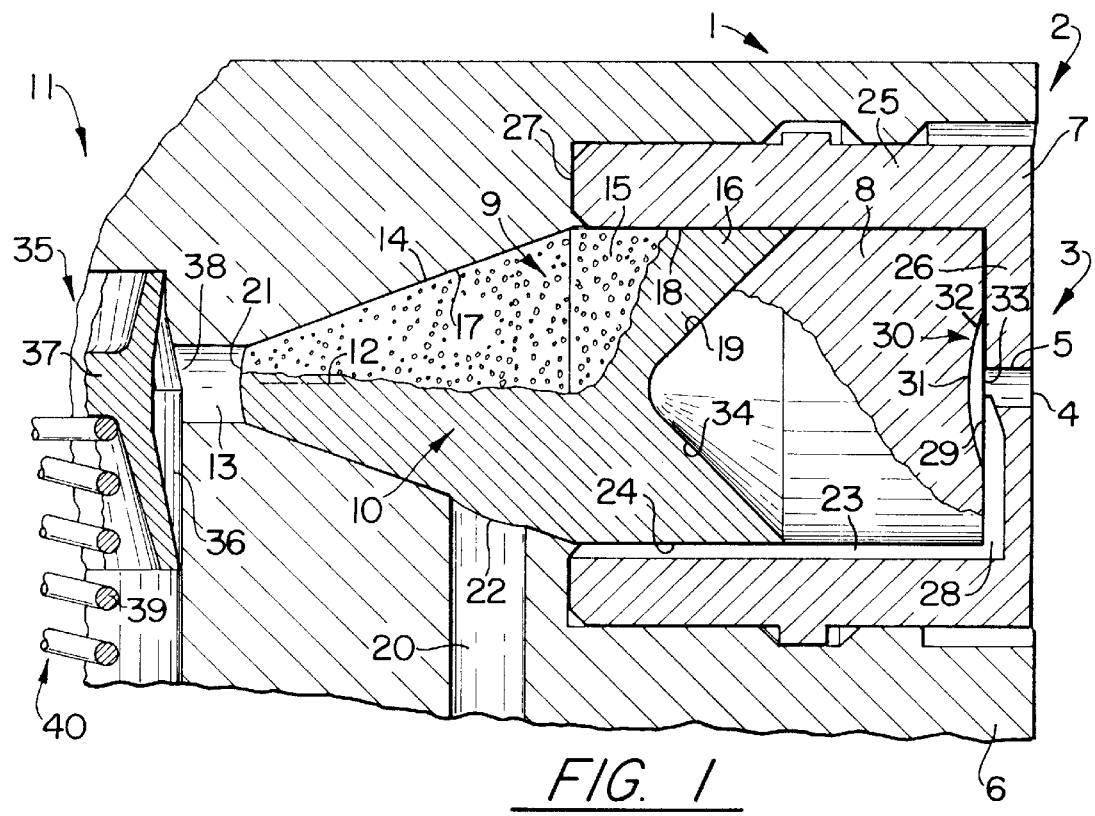
Figures 2, 6:
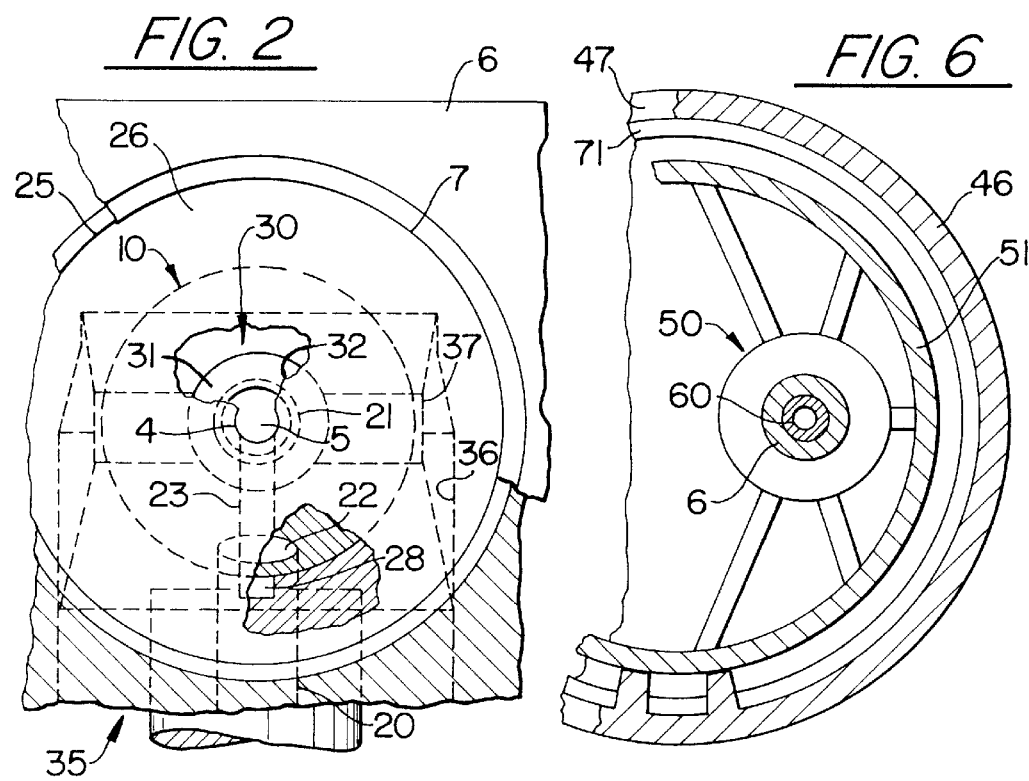

United States Patent

Zuckschwerdt et al.

[11] Patent Number: 5,816,504
[45] Date of Patent: Oct. 6, 1998

[54] DISCHARGE APPARATUS FOR FLOWABLE MEDIA

[75] Inventors: Friedrich Wilhem Zuckschwerdt; Reinhold Jäger-Waldau, both of Radolfzell, Germany

[73] Assignee: Ing. Erich Pfeiffer Gmbh, Radolfzell, Germany

[21] Appl. No.: 586,753

[22] PCT Filed: Sep. 24, 1993

[86] PCT No.: PCT/EP93/02602

§ 371 Date: Jan. 30, 1996

§ 102(e) Date: Jan. 30, 1996

[87] PCT Pub. No.: WO95/08399

PCT Pub. Date: Mar. 30, 1995

[51] Int. Cl.⁶ .................................................. B05B 9/04
[52] U.S. Cl. ...................... 239/373; 239/417.5; 239/463
[58] Field of Search .................................. 239/333, 337, 239/338, 340, 343, 310, 311, 432, 590–590.5, 407, 413, 417.5, 461, 463, 373

[56] References Cited

U.S. PATENT DOCUMENTS

| 2,649,333 | 8/1953 | Miller | 239/417.5 X |
| 3,384,103 | 5/1968 | Lansky | 239/388 X |
| 5,110,052 | 5/1992 | Graf et al. | 239/333 |
| 5,147,087 | 9/1992 | Fuchs | 239/333 |
| 5,295,628 | 3/1994 | Zuckschwerdt | 239/590.5 |

FOREIGN PATENT DOCUMENTS

| 4011537 | 10/1991 | Germany . |
| 4015367 | 11/1991 | Germany . |
| 4102632 | 8/1992 | Germany . |
| 89/00085 | 1/1989 | WIPO . |
| 89/00086 | 1/1989 | WIPO . |

*Primary Examiner*—Lesley D. Morris
*Attorney, Agent, or Firm*—Quarles & Brady

[57] ABSTRACT

A discharge apparatus (1 or 41) for media to be atomized in ultrafine form has a discharge nozzle (3) with a sponge-like medium receiver (10), into which issue on the one hand a functionally closed source unit (50) for the medium and on the other a conveying or delivery device (11) for compressed air, so that by a control mechanism (40) initially a drop of medium spreads out in capillary manner in the receiver (10), after which by random actuation an air pressure surge flows through the receiver (10) towards the medium outlet (4). The medium is discharged from the medium receiver (10) in an already finely divided state, whirled up and once again is finely atomized in the vicinity of an impact atomizer (30) until it passes into the open with a minimum droplet size of max. 2 μm.

46 Claims, 8 Drawing Sheets

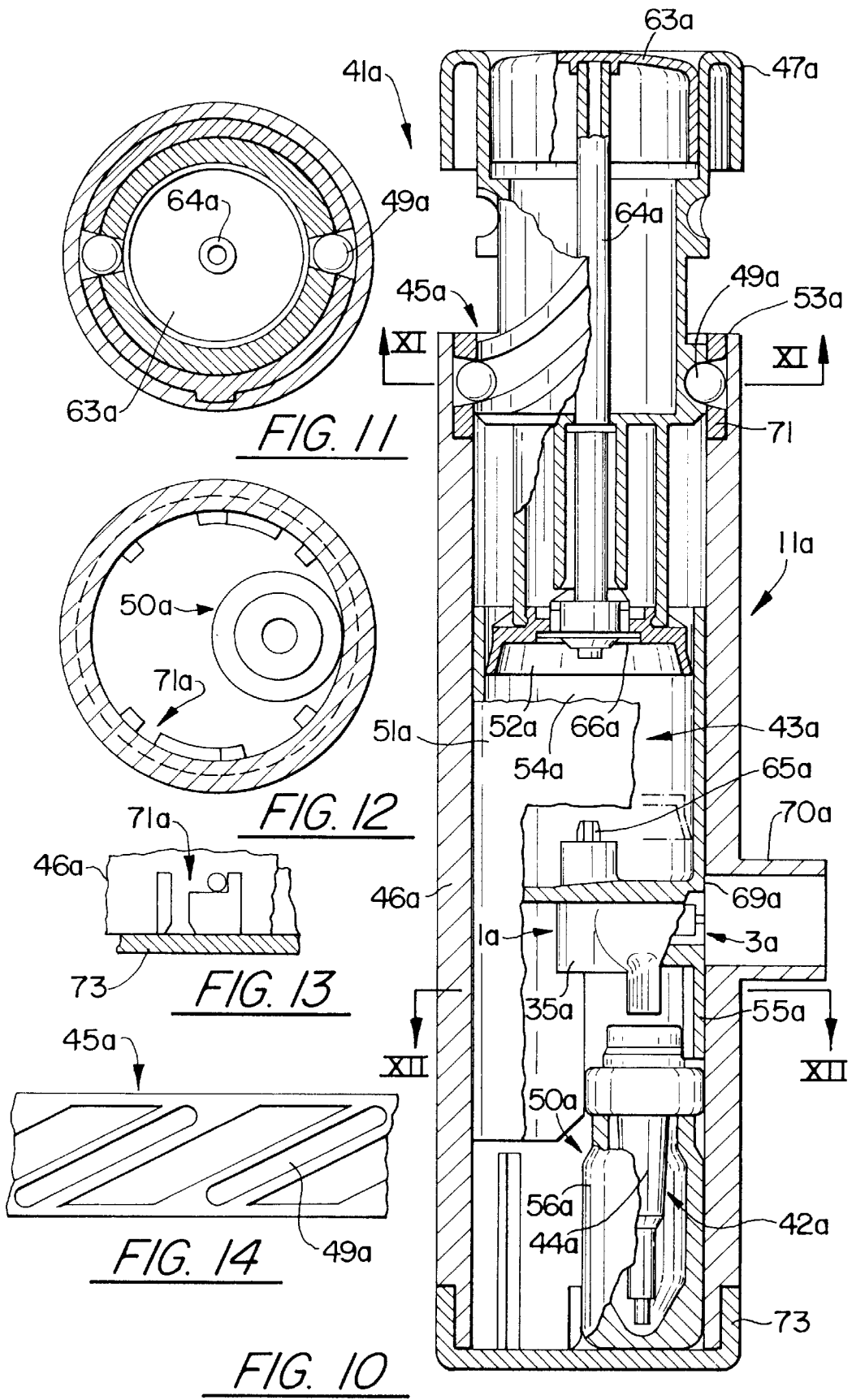

DISCHARGE APPARATUS FOR FLOWABLE MEDIA

BACKGROUND OF THE INVENTION

1. Field of the Invention

The invention relates to a discharge apparatus, which in particular through manual enclosing is free and optionally, without externally supplied lines, can be carried or operated with one hand. The discharge apparatus is to be suitable for the discharge of one or more media, whereof same can be liquid, gaseous, pulverulent, pasty and/or highly volatile and the like.

2. Description of Related Art

Such discharge apparatuses can e.g., according to DE-OS 4,015,367, have one or more external or internal discharge heads and can be intended for discharging at least one medium in an extremely fine distribution. This is e.g. desired when discharging active inhalation substances, so as to give asthmatics a very rapid amelioration for a minimum dose. Ultrafine distributions of non-gaseous active substances in a gas or air or liquid flow as the carrier flow are also required for many other applications, e.g. if two or more separate active substances are to be very homogeneously mixed and then discharged.

Relatively easily flowable active substances can e.g. be gradually finely distributed over a flow path in one or more atomizing stages by means of atomizer nozzles, centrifugal chambers, impact atomizers, whirl atomizers, etc. and can be broken down stepwise into finer particle sizes, but generally particle or droplet sizes below 10 $\mu$m cannot be obtained.

SUMMARY OF THE INVENTION

The object of the invention is to provide a discharge apparatus for media permitting the obviating of disadvantages of known constructions of the aforementioned type and which in particular ensures a very simple breaking down or decomposition of at least one non-pure, gaseous medium into an ultrafine form and/or ultrasmall particle sizes.

In the case of a discharge apparatus comprising one or more discharge heads, e.g. discharge nozzles, which is intended for connection to at least one medium dispenser, this object can be achieved in that means are provided through which at least part of at least one discharge charge provided for a discharging process and formed from one or more media can be made available in one or more medium reservoirs in a spread out distribution and virtually in a rest state and through which then the thus prepared medium can be exposed to a further, again commencing flow, through which the already finely divided medium, as a function of requirements, can be even more finely divided or brought into an even finer form. Fine distribution in the medium receiver is understood to mean a distribution such that the medium, as a result of its physical characteristics, forms the thinnest possible, just still coherent coating, which in the case of a liquid corresponds to a liquid film and in the case of a powder has a thickness corresponding to a maximum of one to ten or twenty times the particle size. Rest state is understood to mean a completely stationary state in the medium receiver or a movement based on a flow energy which is smaller than that necessary in order to convey the medium into the open from the discharge apparatus.

Thus, as a result of its creeping capacity, e.g. a liquid medium at the start or during the further flow can perform a relatively slow spreading movement, which only stops when it is in equilibrium with the cohesive stress with which the liquid film adheres to the corresponding surface of the medium receiver. Therefore the discharge apparatus can operate in a similar manner to a surface gasifier and appropriately there is not a single, through, smooth surface, but instead a spatially distributed surface structure, whose individual micro-surface areas are so distributed and so pass into one another that a medium flowing through the receiver body acts substantially on all sides thereof. Thus, with a minimum space volume there is a maximum surface extension as an adhesive base for the medium to be introduced first.

As a function of the characteristics of the fluid, e.g. the viscosity, or as a function of the desired discharge characteristics, the discharge ratio can be varied within a relatively wide range, particularly with regards to the quantity ratios optionally varying during discharge between the medium to be introduced first and the secondary medium or gas. For example, the medium receiver may be filled with the first medium only to roughly a third of its maximum reception capacity. However, a much smaller secondary medium quantity compared with the first medium can be delivered in a single discharge process, e.g. if at the outlet the medium is to pass into the open in the form of a closed drop, instead of in ultrafine atomized form. The characteristic of the flow of the secondary medium can be so chosen that at the end of the primary medium discharge a small amount of secondary medium afterflows under pressure, so that any plugging closed of the outlet by the primary medium is completely detached in sudden manner from the discharge nozzle or can be passed into the open with a relatively low force. The medium receiver appropriately has a repelling action with respect to one or all the media, e.g. is water-repelling in the case of an aqueous primary medium, so that a very low energy detachment of this medium from the medium receiver is ensured. For example, the medium receiver can be provided with a corresponding repelling coating of polyurethane foam or the like.

With correspondingly small passage spacings between adjacent surfaces of the medium receiver, there can also be a through, crosslinked capillary structure, which ensures that an at least partly liquid medium without any externally supplied delivery energy and only due to capillary action is distributed as finely as possible over a correspondingly large area of the medium receiver. The surfaces of the medium receiver can also be formed by fibrous, flat, granular, porous and/or similar structural parts, which appropriately have a thickness of well below 1 mm or 1/10 or 1/100 mm and form portions which are free on at least two, three or four sides. Such a medium receiver can e.g. be formed by a porous hard body, a foam, a nonwoven material, a pack of sieves and/or the like. Appropriately, the wetting faces of the medium receiver are partly or wholly made from a material which repels the medium, so that it tends to adhere in bead-like manner.

Such bodies are e.g. suitable for transforming foamable media into foam, but here are at least used partly not for foam production, but for such media which at a correspondingly high flow rate of the pressure surge are torn away as separate and therefore finely divided particles or droplets from the surfaces and are conveyed on in this form.

It is particularly advantageous if structural parts of the medium receiver are not positionally rigid under the flow forces which occur, but instead move back resiliently in membrane or lamella-like manner so that they can perform oscillations permitting an even finer detachment of the medium introduced first, particularly from the edges of the lamella. The minimum passage cross-sections of the microstructure can be well below the largest particle size to be reached in this distribution stage, so that most particles, following detachment, do not strike one another again in such a way that they could combine to form larger particles.

The mobility of the structural parts also permits the formation of a short wave due to the initial pressure surge with shortwave, increasing and decreasing flow rate, but which after the start of flow can be substantially constant or very slowly decrease in continuous manner. The initial flow pressure can therefore be kept substantially constant for a very long time, namely until the medium has been removed or discharged almost completely from the receiver.

The dividing or atomizing stage formed by the medium receiver can be followed by one or more stages whereof appropriately the particular stage is in the form of an acceleration stage, whirling stage, detachment stage, impact stage and/or the like for the flow. The particular stage can be partly or wholly within the medium receiver or outside the same, so that e.g. two successive stages can be spaced and act in timed manner on the flow. The outflow from the discharge apparatus into the open at the medium outlet can also be in the form of an atomizing stage, namely as an atomizing nozzle, which compared with the flow rate has such a small passage cross-section or such sharp boundary edges, that the flow jet is whirled up substantially over its entire cross-section and/or is released as an atomized conical flow.

The object can be achieved substantially independently of the construction of the discharge head in that in a discharge apparatus which, in addition to the particular discharge head, has a pressure or compressed gas reservoir, an enclosed gas volume is so pretensioned to an elevated pressure that on reaching the maximum pressure it can only start to be discharged in burst-like manner by path-dependent and not pressure-dependent release as a carrier flow. As opposed to a purely pneumatic energy reservoir or an air pump opening in pressure dependent manner, the medium here is pretensioned to a maximum pressure for a carrier flow, and then supplied to the medium outlet under continuous rapid or very low pressure drop, and can directly or indirectly act on at least one of the aforementioned dividing or atomizing stages.

In a preferred embodiment, means are provided in order to pretension the pressure gas volume by a single actuation, and before this, during it or after it, transfer a discharge stage of at least one active substance into at least one medium receiver. The pretensioned pressure gas volume is blocked against expansion, and by manual release of the barrier can only escape through the particular discharge head, so that the active substance already placed there in ultrafine divided form is detached by it in the described manner, taken up and at least at the nozzle outlet broken up into even finer particle sizes.

The discharge apparatus can be elongated with a maximum cross-sectional width of max. 100, 80 or 50 mm and a max. length of 250, 200 or 150 mm, and in the case of an inhaler, the discharge mouthpiece to be introduced into the mouth is appropriately so arranged and shaped that it leads to a position of the discharge apparatus roughly parallel to the mouth. The mouthpiece is appropriately a hollow connection, which is elongated in longitudinal view and which does not participate in flow guidance and instead enables a substantially free spray through the discharge head from the rear end.

These and further features can be appreciated from the claims, description and drawings and the individual features, both alone and in the form of subcombinations, can be implemented in an embodiment of the invention and in other fields and can represent advantageous, independently protectable constructions for which protection is hereby claimed.

BRIEF DESCRIPTION OF THE DRAWINGS

There are shown in the drawings forms which are presently preferred, it being understood however, that the invention is not limited to the precise arrangements and instrumentalities shown.

FIG. 1 is a discharge apparatus as a detail of a discharge head.

FIG. 2 is a detail of the discharge apparatus of FIG. 1 in a view from the right.

FIG. 3 is a supply-independent overall discharge apparatus with a discharge direction according to FIGS. 1 and 2 on a smaller scale.

FIG. 4 is the discharge apparatus of FIG. 3 on a larger scale and partly in section.

FIG. 5 is a detail of FIG. 4 on a larger scale.

FIG. 6 is a cross-section through the linve VI—VI in FIG. 5.

FIG. 7 is a detail of FIG. 5 on an even larger scale and in a different operating position.

FIG. 8 is a cross-section through the discharge apparatus of FIG. 5.

FIG. 9 is a detail of FIG. 4 on a larger scale and in a modified construction.

FIG. 10 is a further discharge apparatus in a representation corresponding to FIG. 4.

FIG. 11 is a cross-section through the line XI—XI FIG. 10.

FIG. 12 is a cross-section through the line XII—XII in FIG. 10.

FIG. 13 is a detail of FIG. 10 in a developed representation.

FIG. 14 is a further detail of FIG. 10 in a developed representation.

FIG. 15 is the discharge apparatus of FIG. 10 on a larger scale and in a further operating position.

FIG. 16 is a detail of FIG. 10 on an even larger scale.

DETAILED DESCRIPTION OF THE PREFERRED EMBODIMENTS

The discharge apparatus of FIGS. 1 and 2 is substantially formed by a discharge head 2 or a discharge nozzle 3 with associated line or channel connections and is provided to discharge at least one medium from a single, approximately linearly oriented medium outlet 4 in such a way that it leaves the discharge apparatus 1 at said outlet 4. The medium outlet 4 is formed by a short nozzle or end channel 5 with a width which is below 1 or ½ mm. Between its ends or up to the medium outlet 4, the smooth-walled end channel 5 has through, approximately constant passage cross-sections. Its length is roughly one to three times its width or said length is smaller than two or three times said length and both ends are bounded by flanks in sharp-edged manner and which in axial section at the inner end are approximately at right angles or at acute-angles to one another if the channel 5 is widened to the outside. Appropriately an outermost longitudinal portion of the channel 5 is conically widened by approximately 90° to 120° and is therefore shorter compared with the narrowest width of the channel 5 and the flanks at the outer end are at obtuse angles to one another.

The discharge apparatus 1 has a body 6 with a reception opening on the medium outlet side, into which is inserted a cup-shaped nozzle cap 7 in such a way that it is fixably positionally secured with the outer circumference of its jacket by frictional connection and/or positively by a snap connection and is located in substantially countersunk manner within the body 6. Completely within the nozzle cap 7 is provided a core body 8, to whose rear end is connected a filling body 9 projecting from the nozzle cap 7.

Over essentially its entire extension the filling body 9 has an openpore, microporous and elastically displaceable capillary or network structure of through, one-piece, interconnected structural parts, which in the same way as a foam sponge form a cohesive, ultrafine channel or chamber system passing over all the cross-sections and up to all the peripheral surfaces. By shaping or compressing or internal pressurization with a fluid the cross-sections, volumes and/or shapes of these microchannels or microchambers are modified, namely increased and/or decreased and optionally partially closed. Simultaneously this microstructure forms on the entire peripheral surface of the medium receiver 10 grid-like, ultrafinely divided microoutlets for the medium, which are closed over most of the peripheral surface by guide boundary surfaces or compression of the structural material.

The medium receiver 10 forms a positionally fixed chamber system in the flow path between a conveying device 11 and the medium outlet 4 in such a way that all the medium delivered by the conveying or delivery device 11 must flow through the receiver 10 before reaching the outlet 4. Instead of being laterally displaced or at an angle thereto, it is located in an axis 12 of the discharge nozzle 3, in which are also provided the medium outlet 4, nozzle cap 7 and core body 8. The conveying device 11 is connected by means of a pressure surge channel 13 located in the axis 12 to the medium receiver 10, whose passage cross-section is larger than that of the medium outlet 4 or all the channel portions located between the receiver 10 and the outlet 4.

The medium receiver 10 is connected to the channel 13 and over its entire width with an end face which is roughly equally large as the cross-section of the channel 13 and from which the receiver 10 continuously increases in its cross-sections in that it here forms an acute-angled, frustum-shaped end portion 14, whose length is at least as large or larger than its average or central width. To the other end of the portion 14 is connected a short portion 15 with constant full cross-sections, which is substantially cylindrically bounded at the outer circumference, has the same external width as the further end of the portion 14 and a length between about $\frac{1}{3}$ and $\frac{1}{4}$ of its external width. To the end remote from the portion 14 of said portion 15 is connected a portion 16, which with increasing distance from the portion 15 has decreasing ring cross-sections in that its inner circumference increases in the manner of an approximately right-angled pointed cone with spherical segmental, rounded apex or tip. The external width of the portion 16 is approximately the same as that of the portion 15, so that said two portions continuously pass into one another at the outer circumference. The inner circumference of the portion 16 passes conically into its outer circumference, so that its cross-sections decrease to zero.

Over most of its circumference and length, each portion is located on hard-wall boundaries 17,18,19 of the body 6, the nozzle cap 7 or core body 8 in a substantially full surface manner and under pretension. The boundary 17 of the body 6 engaging on the outer circumference of the portion 14 is approximately frustum-shaped and passes with its narrower end directly into the associated end of the channel 13. The further end of the boundary 17 is connected approximately to the inner circumference of the nozzle cap 7, which forms the substantially cylindrical boundary 18 for the outer circumference of the two portions 15,16. Also on the side remote from the channel 13 the medium receiver 10 with its frontal inner circumference engages on a boundary 19, which is formed by the rear, approximately pointed cone-shaped end of the core body 8. In the relaxed state this front face of the receiver 10 can be approximately planar, so that only by pressing in the boundary 19 under local compression of the microstructure does it acquire the described shape. Correspondingly the portion 14 in the relaxed state can have slightly larger widths or a larger cone angle than the boundary 17, so that between the tip of the boundary 19 and the channel 13 there is a core area of the receiver 10, which is at least slightly compressed compared with the surrounding areas.

The narrowest end of the medium receiver 10 bridging and having the same width as the outlet of the channel 13 forms a pressure surge inlet 21. As the medium receiver 10 is not supported here, it can curve inwards into the channel 13 when relaxing, so that the structural openings located at the inlet 21 are slightly widened and there is consequently a correspondingly increased specific inlet cross-section per surface unit. In the outer circumference of the portion 14 issues, transversely to the axis 12, a medium channel 20 provided like the channel 13 in the body 6 and whose through, constant passage cross-sections are roughly the same as those of the channel 13 and therefore have a corresponding relationship to the remaining channel portions. The radial channel 20 is closer to the portion 15 than the inlet 21 and traverses the boundary 17 in such a way that here a medium inlet 22 is formed, which in the manner of a closure is bridged by the outer circumference of the portion 14. The passage cross-section of the inlet 22, whose width can be approximately 1 mm, is much smaller than the largest flow-free passage cross-sections of the medium receiver 10 and the inlet 22 only extends over $\frac{1}{5}$ to $\frac{1}{15}$, particularly $\frac{1}{10}$ of the circumference and over only approximately $\frac{1}{5}$ to $\frac{1}{3}$, particularly approximately $\frac{1}{4}$ of the length of the portion 14. Here again the receiver relaxes under the described expansion of the microstructure into the channel 20.

The outer circumferences of the portion 16 form, virtually over their entire joint length, a receiver outlet 24 for the medium, which in strip-like manner is roughly parallel to the axis 12 and extends over the outer circumference of the portions 15,16 by a part which is at a maximum as large as the inlet 22 or is $\frac{1}{3}$ smaller than the latter. The outlet 24 and the inlet 22 are located on the same side of the axis 12. The axes of inlets 21 and 22 and of outlet 24 are located in a common axial plane of axis 12. This axial plane is parallel to the drawing plane of FIG. 1. Also in the vicinity of the outlet 24 the medium receiver 10 can relax and therefore on the associated surface a slightly widened microstructure is formed. The outlet 24 extends approximately from the wider end of the portion 15 to the wider end of the boundary 19 and there can also be two or more approximately uniformly circumferentially distributed outlets 24.

The outlet 24 is formed by one end of a nozzle channel 23, which is in turn formed by a longitudinal groove on the inner circumference of the jacket 25 of the nozzle cap 7 and passes from the inside from its end wall 26 to the rear end 27 of the jacket 25. On the open groove longitudinal side the longitudinal groove is closed in the vicinity of the outlet 24 by the receiver 10 and immediately following this by the outer circumference of the core body 8, so that the nozzle channel 23 over its entire length forms a circumferentially closed channel. Its through, substantially constant passage cross-sections are significantly smaller than those of the inlet 21 and compared with the increasing, larger passage cross-sections of the portions 14,15 and the connecting part of the portion 16. Thus, there is a significant flow acceleration and a strong flow turbulence from the medium receiver 10 into the medium outlet 24 and into the nozzle channel 23.

With its planar, end face connected in ring disk-like manner to the outer circumference and remote from the medium receiver 10, the core body 8 is permanently fixed in approximately full surface manner to the inside of the end wall 26. This end face is formed by an end portion with an approximately constant outside width of the core body 8 and to the rear end of said portion is connected the shorter portion forming the boundary 19, the sloping boundary 19 extending up to the outer circumference of the front end portion. The longitudinal portion of the nozzle channel 23 at the front end passes via an approximately right-angled deflection 28 into a shorter transverse portion positioned radially to the axis 12 and which is formed by a corresponding groove on the inside of the end wall 26 and is closed on the open groove longitudinal side by the end face of the core body 8. The width of this transverse portion can be roughly the same as that of the longitudinal portion and the depth is somewhat greater, so that here, as a function of requirements, there are slightly enlarged or reduced passage cross-sections or correspondingly a slight reduction or increase in the flow rate. The transverse portion end remote from the longitudinal portion forms a directional nozzle 29 directed against the front end face of the core body 8 and from which the medium flow passes at least partially counter to the main flow or discharge direction of the discharge nozzle 3 and/or at least partially transversely or in inclined manner to said direction. The outlet cross-section of said directional nozzle 29 can be approximately the same as the passage cross-sections of the end channel 5.

In the vicinity of the outlet of the directional nozzle 29 or the inner end of the end channel 5 is provided an impact atomizer 30, against whose cup-shaped, depressed or countersunk impact surface 31 is directed the directional nozzle 29. The impact surface 31 is provided in the form of a central depression located roughly in the axis 12 in the front end of the core body 8 and is connected to the inner circumference of the associated ring-like end face by the outer circumference of its obtuse-angled, frustum-shaped jacket. The bottom face of the impact surface 31 is approximately planar, is approximately at right angles to the axis 12 and in a view is parallel to the axis 12 over and beyond the inner circumference of the inner end of the end channel 5. Through the impact surface 31 and the inside of the end wall 26 closing it in cover-like manner, is formed a gap-like, thin disk or centrifugal chamber 32, whose greatest thickness is only one or a few tenths or down to ½ of a tenth of a millimeter, said thickness constantly decreasing to zero up to the outer circumference. This centrifugal chamber 32 is open at a single outlet 33 located roughly in its central axis and which is formed by the inner end of the end channel 5 and is less than ½ or ⅓ as wide as the width of the chamber 32. Immediately adjacent to the outer circumference of the outlet 33 is located the directional nozzle 29, which either does not or only slightly traverses said outer circumference on the associated side of the axis 12, so that part of the medium flow passing out of the nozzle 29 is directed transversely over the outlet 33 and along the inside of the end wall 26. In cross-section the boundary of the directional nozzle 29 can form a sharp or acute-angled tip with that of the outlet 33 and which is roughly in the plane of the remaining outlet 33, so that here turbulence can be increased. The centrifugal or turbulence chamber 32 is free from inner bodies, is located behind the end channel 5 or the end wall 26 and has in the manner of a parabolic mirror an action focusing reflecting the flow onto the outlet 33 and the jet impacting in the outlet 33 breaks through the jet entering from the directional nozzle 29.

The boundaries 17,18,19 also form guidance or baffle surfaces for the medium and in particular the boundary 19 can form an impact or baffle surface 34 through which the medium is passed to the outlet 24. Through the cross-sectional shape of the portion 16 the receiver 10 forms cross-sections tapering in funnel-shaped manner towards the outlet 24 and its specific structure passage cross-sections to the outlet 24 can be wider and at the medium outlet 24 there is a grid-like distribution of microopenings, which are bounded from the free or exposed structural parts or separated from one another in membrane or fibre manner. Thus, with increasing distance from the baffle surface 24 or the boundaries 17,18 lower flow resistances occur, but there are increasing flow rates towards the outlet 24 within the receiver 10.

As a function of the viscosity and other physical characteristics of the medium to be discharged the receiver could be formed solely by boundaries of a cavity, e.g. corresponding to the boundaries 17,18 or 19 and would therefore be substantially flat. For further features and effects of such a discharge apparatus reference is made to U.S. Pat. No. 5,295,628.

For influencing or controlling the pressure surge supplied by the channel 13, preferably separately from the channel 20 of the receiver 10, a valve 35 is provided, whose main axis is appropriately at right angles to the axis 12 and/or is located therewith in a common axial plane. The valve 35 has in a chamber 36 connected to a pressure source an axially displaceable valve body 37, which runs with two remote, frustum-shaped sealing lips in sealed manner on the inner circumference of the valve chamber 36. This inner circumference is traversed by a chamber outlet 38, which is formed by the rear end of the channel 13 and has a spacing from the inlet 21, which is at the most three to five times the greatest width of the channel 13 or is roughly the same or smaller than said width. The chamber outlet 38 in the outlet position of the valve 35 is closed by the valve body 37 and is located between its valve lips and the valve body 37 is loaded to the stop-limited starting position by a valve spring 39. For further details and effects of the valve 35 and its arrangement reference is made to DE-OS 4,011,537. The valve 35 is a component of control means 40 through which is fixed the operating sequence of the discharge apparatus 1.

Firstly the channel 20 and the inlet 22 are used for supplying the medium receiver 10 with a drop of liquid active substance which, as a result of the capillary action, is propagated from the inlet 22 into the interior of the receiver 10, propagation also taking place towards the inlet 21 and outlet 24. The dosed substance volume can be below the saturation limit of the receiver 10 or so low that the capillary action is ended before the substance has spread over the entire volume of the receiver 10 or up to the areas of the boundaries 17,18 opposite to the inlet 22. At the start, during and/or after the end of this spread or propagation the valve 35 is opened in that the one sealing lip of the valve body 37 is displaced over and beyond the chamber outlet 38, which is therefore in direct line connection with that part of the valve chamber 36, which is permanently line-connected to a pressure chamber, which in this functional phase is under a maximum pressure and whose maximum reception volume is at least 100 to 200 times as large as that of the medium receiver 10 or the valve chamber 36.

It is possible to perform the pressure surge at least partly with a liquid or readily volatile or evaporating medium, optionally through the channel 22, but it is preferably obtained with a compressible medium such as air or another gas and exclusively via the inlet 21, while the inlet 22 is substantially closed, e.g. by valve closure of the channel 20 or in that its narrowness with respect to the flow cross-sections in the receiver 10 acts in much the same way as a closure. A closure can also be provided by a liquid column in the channel 20. By partial or complete or gradual or sudden rapid opening of the chamber outlet 38 independently of any simultaneous pressure rise in the pressure chamber of the delivery or conveying device 11, the pressure surge medium flows with a more or less burst-like action and with very high flow speed against the inlet 21. This medium can be compressed in the pressure chamber e.g. to at least ⅕ or ⅒ of its relaxed volume. The medium then flows through the at least partially only surface wetted and/or at least partially filled channel structure of the medium receiver 10 at a flow rate which, as a function of the degree of saturation of the receiver 10, is roughly the same, larger or smaller than the flow rate at the inlet 21.

As the pressure surge medium impacts on the inlet 21 and in the interior of the receiver 10 on the structural parts and encounters the active substance, in the receiver 10 there are vibrations to said structural parts, which additionally lead to the tearing away through the flow for the detachment of the substance in the form of very fine droplets. The latter are entrained by the carrier flow in the receiver 10 on numerous, substantially zig-zag paths, which result from the nature of the microstructure and whose main direction is to the outlet 24. As a result of the structural compressions in the vicinity of the boundaries 17,18,19 the flow does not tend to reach these areas and instead remains substantially spaced within the peripheral faces of the receiver 10. In the vicinity of the portion 16 the flow can be given a circular or ring-like rotary flow round the axis 12 and can consequently be supplied to the outlet 24.

Parts of the flow which may reach the baffle surface 34 are passed along the latter immediately to the front end of the outlet 24 into the nozzle channel 23. In the vicinity of said front end the outflow flow rate can be at its highest and drops away rearwards. The rear end of the boundary 19 is spaced upstream of the rear end of the outlet 24 or the portion 15 roughly in the center between the portion 14 and the front end of the outlet 24. The transition between the portions 14,15 can be roughly in the plane of the rear end 27 and the length of the outlet 24 can be at least three to eight, particularly six to seven times longer than the greatest associated width of the nozzle channel 23 or its longitudinal portion, which can e.g. be twice as long as the outlet 24. The transverse portion of the nozzle channel 22 is shorter than the latter or the outlet 24.

The active substance leaves the outlet 24 in the form of ultrafine divided droplets within the carrier flow and which on passing into the nozzle channel 23 is accelerated compared with the flow rate at the inlet. The flow flows along the circumferential edge bounded by the obtuse-angled flanks between the boundary 19 and the connecting portion of the core body 8, in whose vicinity there is a further turbulence, as a result of which and the high flow rate the droplet size here or in the nozzle channel 23 and at the deflection 28 can undergo a further size reduction. The fluid flow then passes out of the directional nozzle 29 at a high speed under different acute and obtuse angles onto the impact surface 31, from where it is reflected partly directly into the outlet 33 and partly against the end or ring face of the turbulence or centrifugal chamber 32 surrounding the latter. As a result of the build-up at the outlet 33, in the chamber 32 there is a relatively high overpressure, under which the fluid flow flows out of the chamber 32 through the outlet 33 and along its sharp edge. Thus, not only through the single or multiple, reciprocating impact in the turbulence chamber 32, but also by flow shearing at the edge of the outlet 33, there is a further decrease in the droplet size. From the highest pressure in the turbulence chamber 32 the pressure decreases from the outlet 33 to the medium outlet 4. This represents the greatest pressure difference in the entire medium guidance. Spaced following the same there is a further reduction in the droplet size on passing out at the sharp edge of the medium outlet 4, which can be outwardly conically widened. It has been found that the droplet size in the conical jet leaving the medium outlet 4 can be reduced to approximately 2 $\mu$m or less and that the largest droplets are max. 10 $\mu$m. Thus, within this range there is a very advantageous size mixture with an average size of about 5 $\mu$m or less.

The discharge apparatus 1 operates in a particularly advantageous manner if it is combined to a structural unit with a discharge apparatus 41 according to FIGS. 3 to 9 which, apart from the compressed air conveying device 11, also has one or more conveying devices 42 for the non-gaseous or liquid medium. Instead of and/or in addition to an externally filled pressure gas reservoir, the conveying device 11 has an air or gas pump 43. Correspondingly the conveying device 42 has a receiver pump 44. Both pumps are operated with a clamping device 45 and are substantially completely encased within an elongated base body 46, which over its entire length has approximately constant outer cross-sections and in the manner of a stick grip can be gripped, carried, operated and correctly used with one hand.

In an axial portion or connected to one end of the base body 46 is provided a handle 47, which essentially forms an extension of the base body 46 with approximately the same outside cross-sections, but can be given a much smaller outside width compared with the base body 46. The handle 47 is cylindrical like the body 46 and serves as an operating member for the clamping device 45 and to this end acts on a clamping drive 49 of a clamping unit 48 in such a way that the handle 47 in each operating position has approximately the same axial position with respect to the base body 46. The clamping drive has a sleeve-like adjusting member with an external thread and which is connected in one piece to the inside of the end wall of the cap-like handle 47 and over which telescopically engages a cap-shaped rotor. This rotor engages with a countermember or internal thread in the rise or pitch member or thread of the adjusting member and closes with its end wall the open end of the adjusting member and projects like the latter over the open front of the jacket of the handle 47 and into the base body 46, is axially displaceable within the body 46 and is prevented from rotating with respect to the latter and in the same way as the handle 47 is positioned in the axis of the body 46 so that the rotor with its outer jacket, except for a ring-like gap, can extend up to roughly the same insides of the jackets of the body 46 and the handle 47. The thread connection can be so constructed with a degressive pitch that the gearing down of the handle 47 to the rotor increases with increasing compression in the conveying or delivery device 11. For rotation prevention purposes the base body 46 has on the inside of its jacket one or more longitudinal grooves, which are appropriately in each case formed by two parallel, juxtaposed axial webs and in which the rotor engages with at least one sliding cam, which is appropriately located in the vicinity of the front end in the clamping direction. The end wall of the handle 47 also forms the associated outermost end of the overall discharge apparatus 41.

The receiver pump 44 belongs to a dispenser or source unit 50, which is inserted or replaceable as a closed structural unit in the base body 46. The source unit 50 is displaceably arranged on an at least partially, sleeve-like clamping body 51 having roughly the same outside width as the rotor, so as to be displaceable by a maximum stroke or travel of the pump 44. The clamping body 51 is connected with one end approximately to the rotor of the clamping drive 49, extends over the entire length of the source unit 50, over the associated extension of the connecting discharge apparatus 1 and over the length of the axially thereto connected gas pump 43, whose cylinder 54 it forms with the outermost end remote from the drive 49. The inside width of the clamping body 51 or the cylinder 54 also roughly corresponds to that of the rotor and is therefore only smaller than the inside width of the base body 46 by the necessary wall thicknesses and axial guide. The clamping body 51 is axially displaceably secured so as not to rotate with respect to the base body 46 in the manner already described relative to the rotor, the sliding contact substantially only taking place in the vicinity of the longitudinal edge faces of the axial webs and is exposed to a limited sliding friction. The rotation preventing cams of the clamping body 51 are located in the vicinity of its end remote from the clamping drive 49. The body 6 of the discharge apparatus 1 is fixed within the envelope surface of the clamping body 51 and constructed in one piece with an intermediate or end wall, which in spaced manner between the ends of the clamping body 51 divides the cylinder 54 from the partly open space in the jacket area and which receives the source unit 50.

From the end remote from the clamping drive 49 and open to the full cylinder width of the clamping body 51 engages in the cylinder 54 a ring disk or cup-shaped piston 52, which on its outer end is connected to a sleeve-like piston shaft, which in one piece projects from the inside of an end wall 53 of the base body 46. The end wall 53 forms the end of the overall discharge apparatus 41 remote from the handle 47 and is constructed as a ring-like bottom in one piece with the cup-shaped base body 46, with respect to which the piston 52 is always axially substantially fixed.

Roughly equiaxially to the through, linear medium channel 20, which is also axially parallel to the discharge apparatus 41 is connected at its end remote from the axis 12 or medium receiver 10 a plug-in and sliding connection 55, in which the source unit 50 is secured in radially approximately clearance-free manner, but can be reciprocated axially by a predetermined amount.

The dispenser unit 50 has at its end remote from the sliding connection 55 a receiver reservoir 56 e.g. in the form of a small bottle running axially parallel to the discharge apparatus 1 or in the axis of the channel 20 and whose bottom remote from the sliding connection 55 is formed by a drag piston 57. The receiver pump 44 projects through the neck of the reservoir 56 over most of its length into the latter and with its inner end into a cup-shaped depression of the drag piston 57 closely adapted to the reservoir 56. The receiver pump 44 is e.g. fixed by a crimp ring or the like to an outer face of the neck of the reservoir 56 and is consequently fixed in sealed manner thereto. The receiver pump 44 is constructed as a thrust piston pump, has at its inner end an inlet with an inlet valve 58 constructed as a self-locking overpressure valve and contains a piston unit 68, which forms a pressure and/or path dependent opening outlet valve 59 self-closing under spring loading. For this purpose a central shaft of the piston unit 68 forms a ring-like valve seat and a sleeve-like pump piston a valve body axially movable with respect thereto, as well as in its interior an outlet channel through which can pass the medium from the pressure chamber of the pump 44 through the pump piston into a ram 60.

This ram 60, which displaceably traverses a cylinder cover of the casing of the receiver pump 44 located outside the reservoir 56 projects with its outer end into the body 6 with which it can be connected by means of an axially securing plug, clamp and/or snap connection in such a way that the outer end of the outlet channel is directly connected to the associated end of the equiaxial channel 20. With its free outer circumference projecting over the crimp ring the cylinder cover simultaneously forms the sliding member of the sliding connection 55. Within the casing of the receiver pump 44 is provided a return spring, which on the one hand forms the spring of the ball or inlet valve 58 and on the other the return spring of the piston unit 68 and consequently the return spring for resetting the source unit 50 with respect to the body 6. The source unit 50 can be fully operated as a discharge apparatus in the removed state by operating the ram 60.

Figure 5:
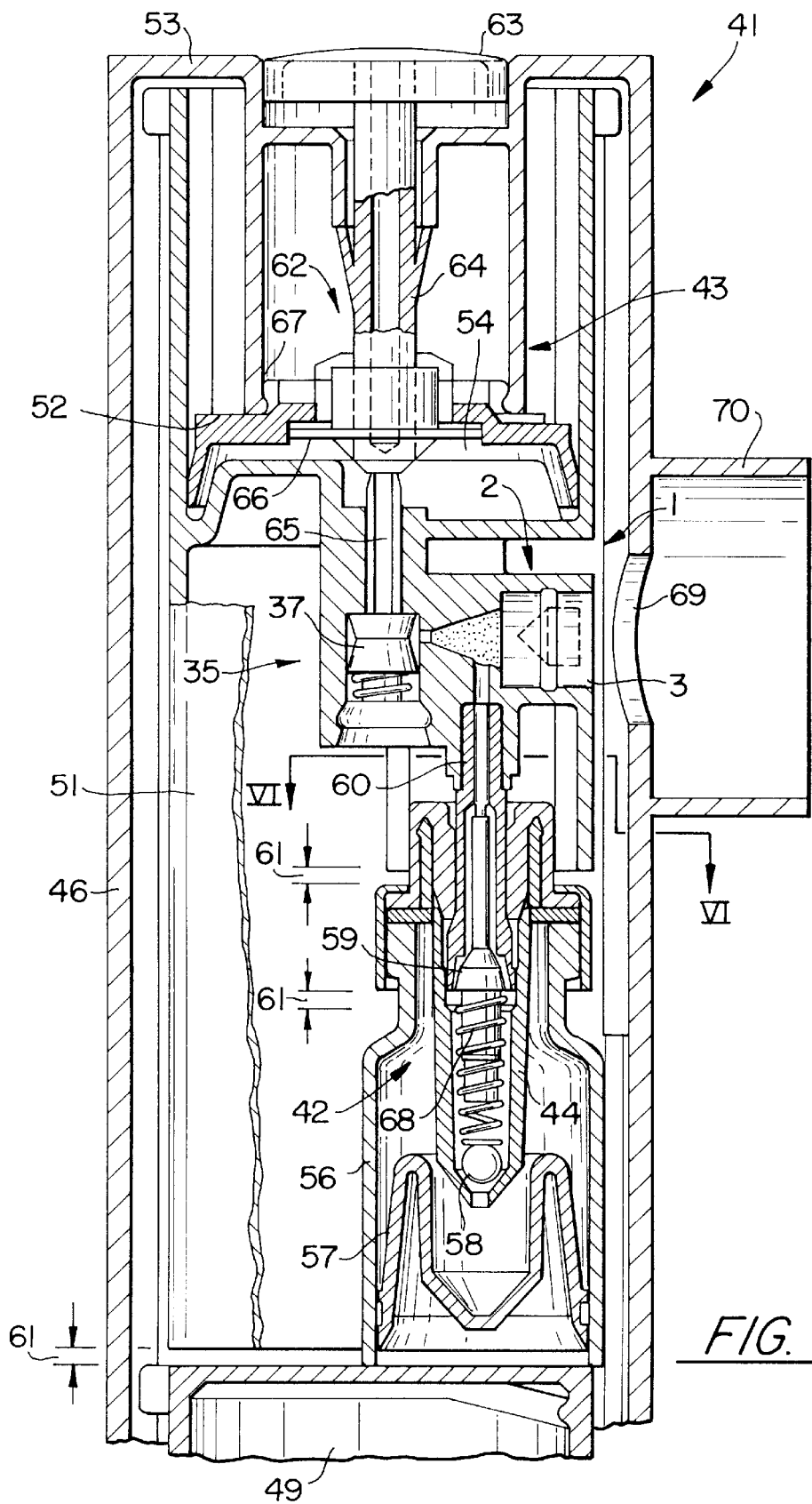
Figure 7:
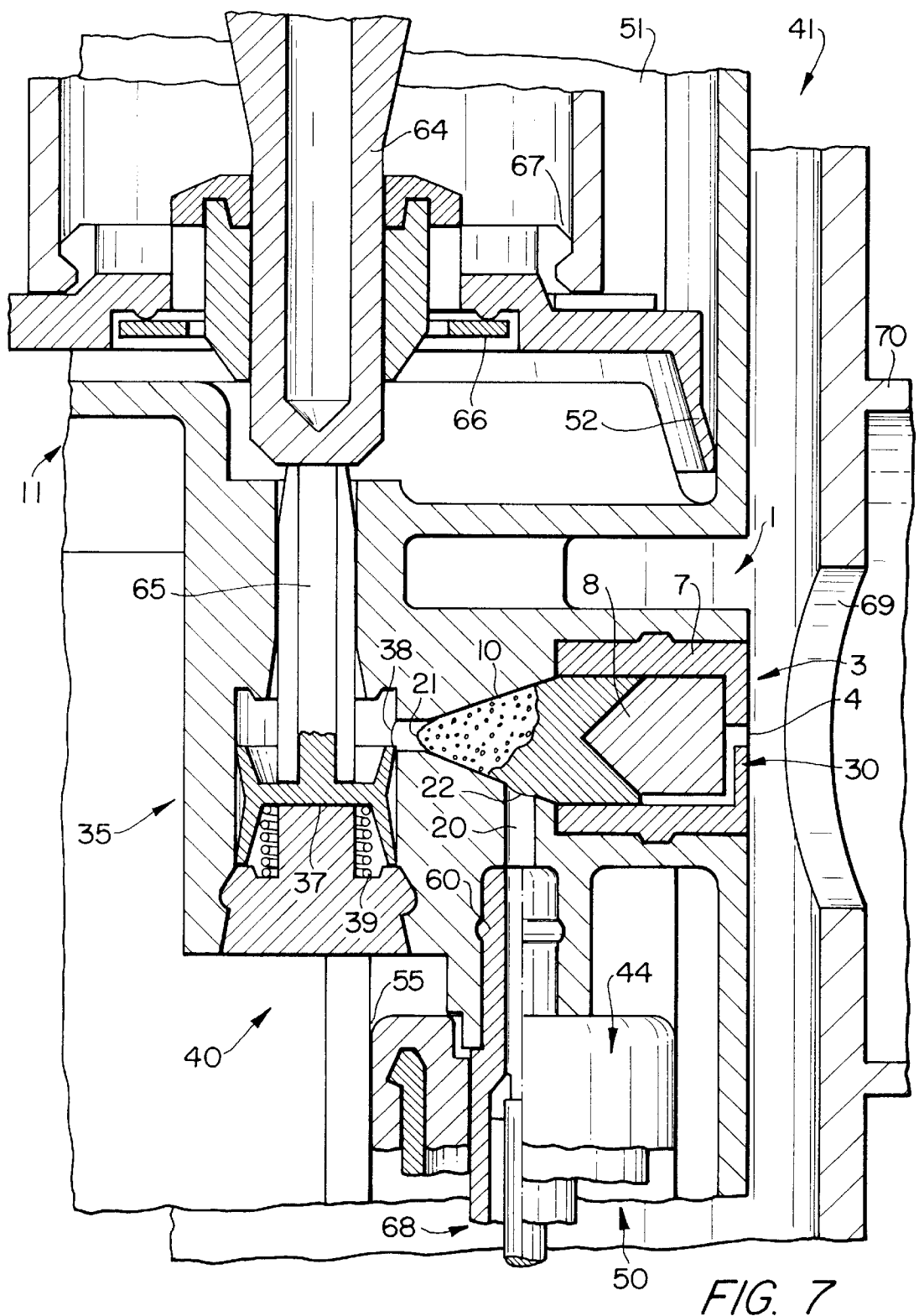

The working stroke of the receiver pump 44 for the discharge of a dosed charge is very small and can e.g. be one or a few millimeters. The source unit 50 is operated by operating the fixing device 45 by said stroke 61, which is shown in FIG. 5 for the movement of the source unit 50 with respect to the sliding connection 55, the movement of the pump piston with respect to the pump casing and the idle path of the rotor of the clamping drive 49 with respect to the clamping body 51. If the handle 47 is rotated relative to the base body 46, then the rotor of the clamping drive 49 is moved axially. As on the outside of the end wall of the rotor engages the associated end of the reservoir 56 or the source unit 50 under the tension of its return spring and the associated end of the clamping body 51 in the starting position has a spacing from its end wall corresponding to the stroke 61, firstly the source unit 50 is axially adjusted relative to the clamping body 51 and consequently performs a pump stroke 61. At the end of the pump stroke the pump piston strikes with its end against an inner ring shoulder of the pump chamber, so that the pump piston is raised from the valve seat and the outlet valve 59 is opened. Thus, from the pump chamber and the outlet channel a drop of medium is discharged into the channel 20 and from there to the inlet 22, after which said drop spreads in the described manner within the medium receiver 10.

Figures 3, 4:
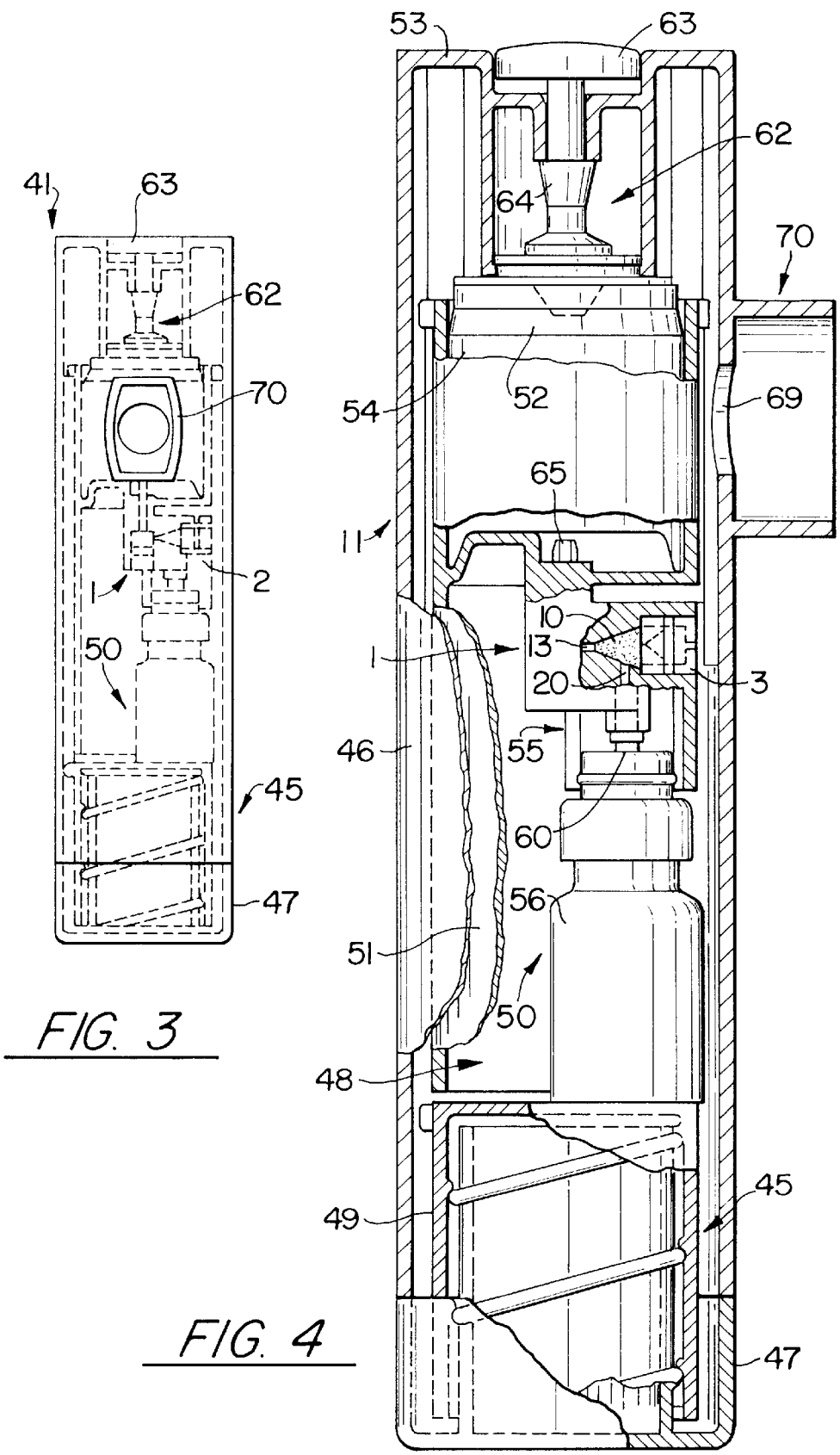

At the end of this pump stroke and in the further course of the actuation of the handle 47 the clamping body 51 is carried along by stop action, while the outlet valve 59 can remain open. The clamping body 51 now directly connected to the end face of the rotor is moved with respect to the piston 52 against the force of the overpressure building up in the cylinder 54 out of the starting position according to FIG. 4 into the end position according to FIG. 5, in which the associated end of the clamping body 51 virtually strikes against the inside of the end wall 53. The clamping member rotor now projects over the adjusting or control member with most of its length. For securing this fixed position, also with released handle 47, the thread of the clamping drive 49 can be constructed in self-locking manner and/or with the rotor can be associated a resilient locking means, which can be overcome by a corresponding powerful turning back of the handle 47, but not by axial pressure on the clamping body 51. In the clamping position the inside of the bottom wall of the piston 52 is at a limited distance from the intermediate wall of the base body 46, which has a cup-shaped construction and engages in the piston 52.

In order now to release the discharge apparatuses 1,41 for a discharge process into the open, a release mechanism 62 is provided, which is operable by a handle 63, by means of a ram 64, which is separate from the handle 47 and is located in the vicinity of the other end of the discharge apparatus 41. The knob or disk-shaped handle 63 is substantially countersunk in a central depression of the end wall 53 and is inserted from the outside with its one-piece ram 64 in a sliding guide in such a way that it is secured against moving back by a snap and barb member located on the ram 64 and is stop-limited in the starting position.

The valve body 37 of the valve 35 has in the axis of the discharge apparatus 41 a valve shaft 65 projecting through the body 6 or the associated end wall into the cylinder 54 and which cross-sectionally is so profiled in cruciform manner, that between its outer face and the bore receiving it are formed one or more longitudinal channels, which permanently connect the cylinder 54 to the inlet side of the valve chamber 36. The inner end portion of the ram 64 traverses in slidable or longitudinally displaceable manner, but sealed in pressure-tight manner by means of a separate, compressed sleeve seal and in spaced form within the associated piston shaft, the end wall of the piston 52 in such a way that the end face of the ram 64 when the handle 63 is in the starting position and the clamping body 51 in the clamped position engages at least approximately on the end face of the valve shaft 65, but the valve 35 is still closed.

If the release mechanism 62 is now operated by finger pressure on the outer face of the handle 63 against the tension of the valve spring 39, the valve 35 opens in the described manner and the compressed air pretensioned in the cylinder 54 escapes via the shaft channels and the valve chamber 36 to the inlet 21 in order to bring about the described functions of the discharge apparatus 1. This process can be broken off or interrupted at any time by releasing the handle 63, because then the latter, like the valve 35, is moved back to the starting position by the valve spring 39. By the choice of the operating stroke it is optionally also possible to continuously vary the passage cross-section of the chamber outlet 38. After complete opening of the chamber outlet 38 the travel is limited by a stop shaft surrounded by the valve spring 39 and which is sprung into the body 6 forming the valve casing on the side of the valve body 37 remote from the valve shaft 65 and forms an abutment for the valve spring 39. This stop shaft is laterally immediately adjacent to the ram 60, which including the source unit 50 is so laterally displaced with respect to the valve or central axis of the discharge apparatus 41 that it is located between said central axis and the medium outlet 4.

An inlet valve 66 of the gas pump 43 forms a structural unit with the piston 52, which forms on the inside of its end wall a valve seat for a ring disk-shaped valve body traversed by the ram 64. The preassembled structural unit formed by the piston 52 and inlet valve 66 is fixed to the associated piston shaft by an axial snap connection 67. After performing a discharge the fixing drive 49 can be moved back to its starting position by rotating back the handle 47. For the corresponding return of the fixing body 51 a positive connection can be provided between the rotor of the clamping drive 49 and the clamping body 51, a compression spring located in the cylinder 54 and/or a return spring located on the outside of the clamping body 51, so that the latter is moved back with the rotor of the clamping drive 49 to the starting position. The receiver pump 44 or its outlet valve 59 are returned to the starting position by the associated return spring.

During the return movement the inlet valve 58 opens and under the automatic moving up of the drag piston 57 from the reservoir 56 a further medium charge is sucked into the pump chamber of the receiver pump 44. Through the automatic opening of the inlet valve 66 constructed as a check valve air is sucked from the outside into the cylinder 54 and, outside the ram 64 and the associated seal, flows through the end wall of the piston 52, the associated piston shaft and the bearing opening for the ram 64 in the end wall 53. Finally, at the start of the return movement the valve 35 closes automatically. Following such a setting of the starting state a further discharge cycle can be performed in the described manner.

As the discharge apparatus 1 is immediately adjacent to the pressure chamber or to the cylinder 54, the line paths between said pressure chamber and the inlet 21 are very short, so that there are very small flow energy losses. Due to the described construction the medium outlet 4 in the starting position is in a different axial position with respect to the base body 46 than in the clamping position. In the clamping position the medium outlet 4 is approximately equiaxial to an approximately flat-oval discharge connection 70 constructed in one piece with the jacket of the body 46 and freely projecting over its outside. Roughly in the axis of the discharge connection 70 the jacket of the base body 46 is provided with an opening or passage 69, which has a smaller width compared with the maximum width of the connection 70, but is sufficiently wide that it does not influence the nozzle jet passing out of the discharge nozzle 3 or is not affected by said jet at its boundaries. The greater cross-sectional extension of the discharge connection 70 is roughly parallel to the longitudinal direction of the discharge apparatus 41, so that the latter is to be oriented roughly parallel to the mouth, when the lips enclose the discharge connection 70. In the starting position the discharge nozzle 3 is axially displaced with respect thereto, i.e. spaced from the connection 70 it is completely concealed and screened within the base body 46 and is protected from dirt. The passage 69 is then substantially closed by the jacket of the clamping body 51. For representation purposes in FIG. 3 the discharge connection 70 is shown displaced by 90° relative to the discharge head 2.

Figure 8:
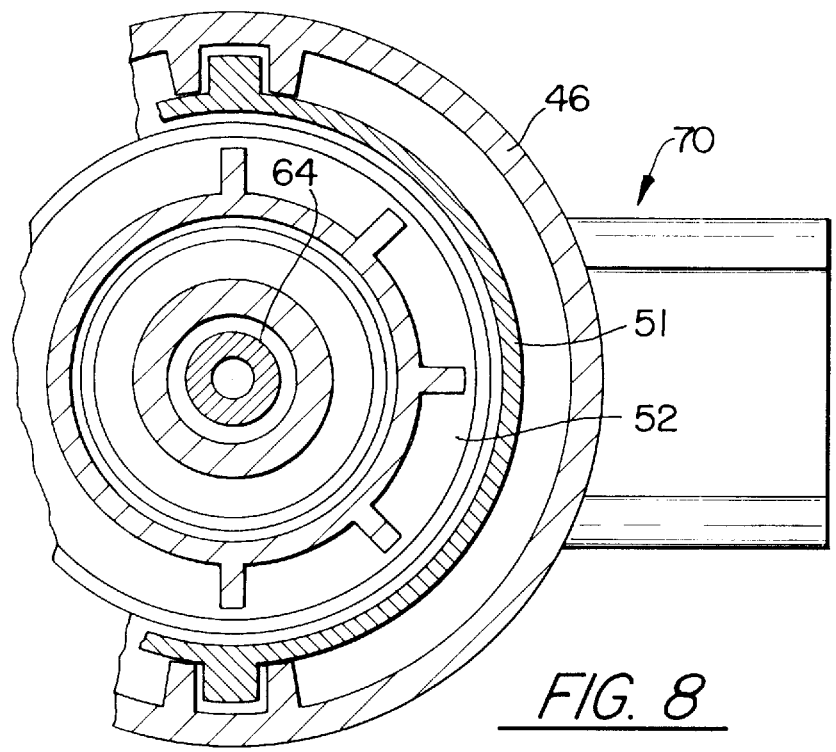

As can in particular be gathered from FIG. 8, the shaft of the piston 52 is stiffened on the outer circumference by radially projecting longitudinal ribs, whereof only part is shown for reasons of simplicity in FIG. 8 and which for reliable pressure supporting purposes extend to the rear face of the elastically resiliently deformable piston 52.

Figure 9:
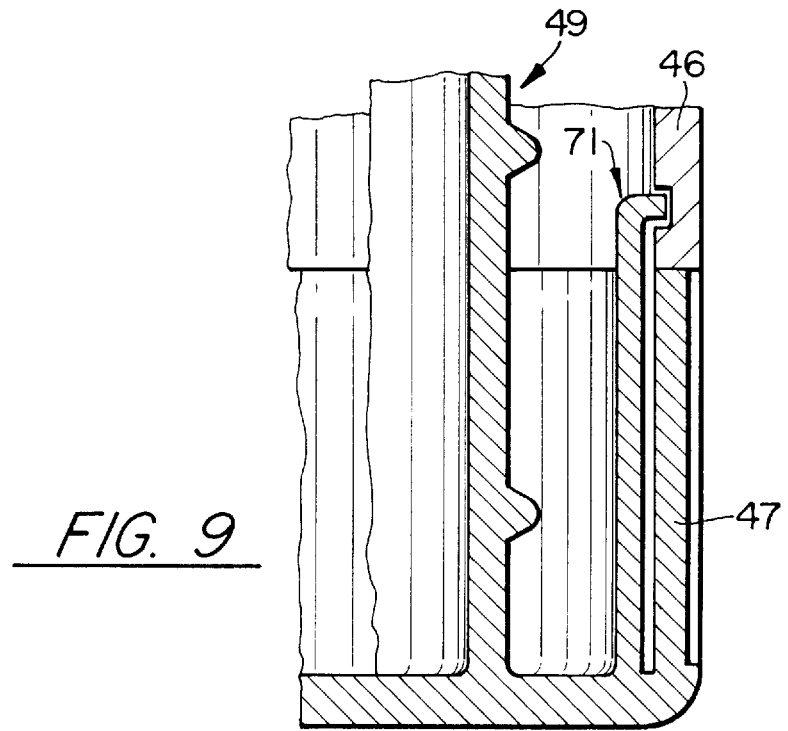
Figure 15:
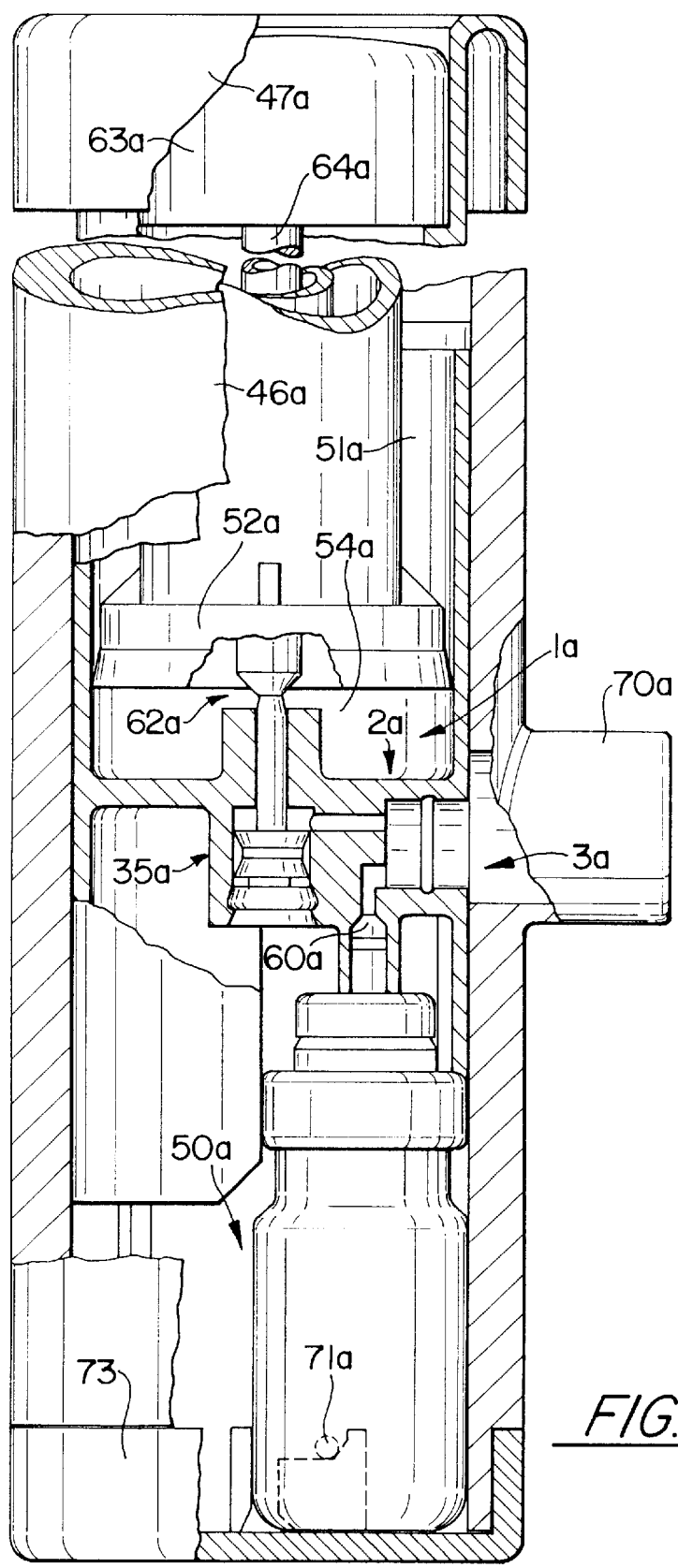
Figure 16:
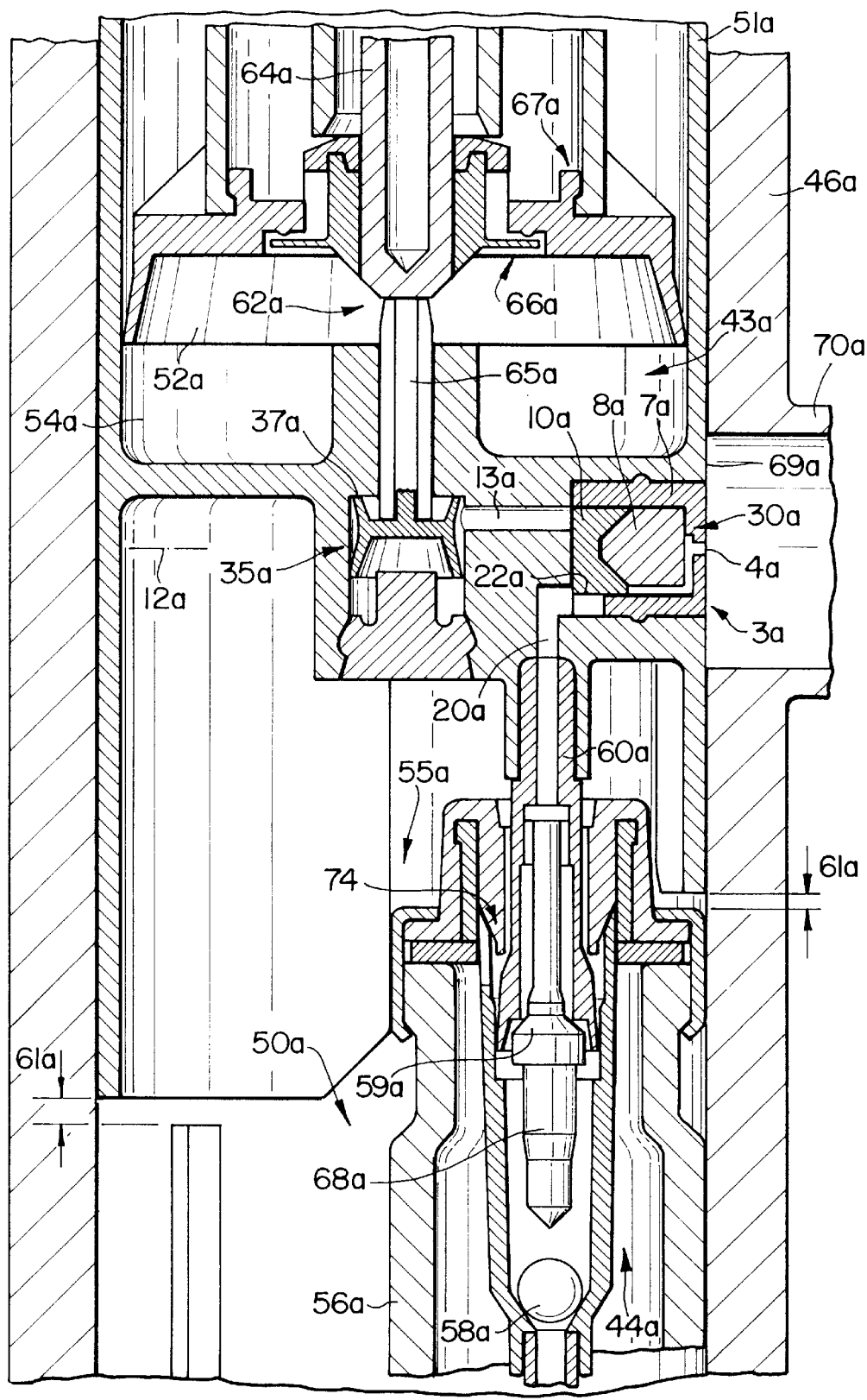

FIG. 9 shows an axial securing means 71 for the handle 47, which simultaneously forms an end or terminating cover for the associated end of the base body 46. The axial securing means 71 can e.g. have a radially resilient inner sleeve, which is located with a limited radial spacing from the inner circumference of the jacket of the handle 47, passes in one piece from the inside from the end wall thereof, projects over the open cap face less far than the adjusting member of the clamping drive 49 located within it and at the free end forms a radially outwardly directed ring flange, which engages in a ring groove on the inner circumference of the base body 46. Thus, a self-engaging snap connection formed solely by axial assembly is obtained, which can optionally be so constructed that by the application of a correspondingly large axial take-off force it is automatically disengaged and thus permits a non-destructive opening of the base body 46.

For assembly purposes the piston 52 can be inserted from the open end of the base body 46 and secured by the axially striking snap connection 67. The preassembled structural unit of clamping body 51, source unit 50 and discharge unit 1 can then be inserted from the open end into the base body 46. It is also conceivable to insert and snap in together with said structural unit the piston 52 already located in the cylinder 54. Before or after the assembly or fitting of the piston 52 or the structural unit, the handle 63 with the ram 64 can be inserted and snapped in from the other end and in the opposite direction. Before or after the insertion of the handle 63, the handle 47 with the preassembled clamping drive 49 can be fitted and is suitable by operating the piston 52 still located in the cylinder 54 for bringing about the locking of the snap connection 67. After the release of the handle 47 the source unit 50 can be axially withdrawn in non-destructive manner from the plug connection 55 and replaced by a new one.

In FIGS. 10 to 16 corresponding parts are given the same reference numerals as in FIGS. 1 to 9, but followed by the letter a, so that all the description parts apply to all the embodiments. The discharge apparatuses 1, 1 a or 41, 41a can be interchanged in the embodiments or provided in a single embodiment, in order to e.g. discharge different media from different medium outlets or for using two or more clamping or fixing devices 45, 45a for pretensioning one or more pressure reservoirs.

The discharge apparatus 1a here has a medium receiver 10a, which terminates substantially flush with the rear end of the nozzle cap 7a and in which issues the inlet of the channel 13a eccentrically to the axis 12a in such a way that it is located on the side of the axis 12a remote from the medium inlet 22a and is approximately adjacent to the inner circumference of the jacket of the nozzle cap 7a. The medium channel 20a issues on the rear, approximately planar face of the medium receiver 10a and/or on a circumferential area connected thereto and for this purpose radially traverses the jacket of the nozzle cap 7a. In the case of the discharge apparatus 1 the medium receiver 10 is longer than the core body 8 and in the case of the discharge apparatus 1a is shorter, so that there is an approximately ring disk and cup-shaped filling body.

Both handles 47a, 63a are here located at the same end 53a of the base body 46a, approximately coaxially in one another and are inserted from the end 53, which is open to the full remaining inside width of the body 46a. The handle 47a has a sleeve-like shaft projecting in one piece from the inside of its end wall and which is provided on its outer circumference with an inside thread-like pitch and following onto the latter passes into an extension, which forms the shaft for the piston 52a. Within the cross-sectionally double ring-shaped handle 47a is located the cap-shaped handle 63a, which in the vicinity of the inside of its end wall is connected by means of a snap connection to the separate ram 64a. In an internally widened end portion of the open end 53a and approximately connected thereto is inserted a sleeve-like cage 71, which carries a number of spherical transfer or rolling bodies corresponding to the number of pitches of the inside thread and which are uniformly circumferentially distributed and engage in the inside thread. Therefore the clamping drive 49a can therefore be fitted as a preassembled structural unit together with the handle 63a, the ram 64a, the piston 52a with the inlet valve 66a and the cage 71 with the transfer members on the base body 46a.

As in this case the handles 47a,63a and the piston 52a perform the axial clamping movement of the clamping device 45a relative to the base body 46a, the adjusting body 51a essentially only performs the stroke 61a of the conveying device 42a. This stroke 61a only takes place when after a correspondingly large stroke of the piston 52a the pressure in the cylinder 54a is so high that, as a result of the corresponding pneumatic force connection, the actuating force is reached which is required for operating the receiver pump 44a. For securing the clamping device 45a in the clamped state, in which the handle 47a approximately tightly closes the open end 53a, a corresponding resilient locking means can be provided. For example, the pitch grooves having a pitch of approximately 30° and shown in the developed view of FIG. 14 can have adjacent to their associated ends locking cams for jumping over through the transfer members in both movement directions, if a correspondingly high actuating force is imparted to the handle 47a.

In this embodiment the discharge apparatus 1a or the source unit 50a can be at least axially substantially fixed with respect to the base body 46a and/or can be fitted from the open end 53a, optionally as a preassembled structural unit. However, the other end of the base body 46a is open to the full inside width and closed with a cap-like cover 73, whose positive axial securing means 71a is formed by a locking system, which can be locked or released by oppositely directed rotation of the cover 73 with respect to the body 46a. The reservoir 56a of the source unit 50 extends with its bottom approximately up to the inside of the end wall of the cover 73, with respect to which the source unit 50a is supported against the axial actuating force during the stroke 61a. Following the non-destructive removal of the cover 73, accessibility is also obtained from its end for inserting or removing the source unit 50a.

The end of the stroke 61a can be limited by the striking of the adjusting body 51a on the base body 46a, e.g. on an inside rib. The sliding guide 55a can cooperate as a sliding face with a larger or the largest outer circumference of the unit 50a, namely with the fastening or crimp ring for the receiver pump 44a and/or with the outer circumference of the reservoir 56a.

The reservoir 56a is in this case formed by a glass or similar bottle closed in one piece and fixed to the bottom and into whose bottom area narrow to form a sump extends the receiver pump 44a with the inlet of a suction or riser tube, which forms the line connection to the inlet valve 58a. Thus, the source unit 50a, also in the unassembled state, forms a system which is closed in pressure-tight manner to the outside by the pretensioned outlet valve 59a and where, even after a long storage period, there is no need to fear bacterial contamination of the stored medium. A vent valve 74 for the storage area and whose two valve closing parts are appropriately formed on the one hand by the pump piston and on the other by the cylinder cover, is also closed in pressure-tight manner under pretension in this starting state.

The circular valve disk of the inlet valve 66a of the gas pump 43a can be constructed in one piece with the sealing muff, through which the ram 64a is passed in sealed manner in the vicinity of the piston 52a. In this case the valve disk projects in ring disk-like manner over the outer circumference of the sealing muff and is resiliently elastically deformable by bending for the valve opening. As is shown in FIG. 1, the inner circumference of the valve chamber 36 can also be stepped in such a way that the chamber outlet 38 is located in a widening and/or widened portion, so that here an inner ring shoulder is formed. In the closed position the valve body 37 engages on the narrower inner circumference, which it leaves in sudden manner on operation with its sealing lip locking the chamber outlet 38 against the pressure in the cylinder 54, so that the through-flow connecting cross-section to the chamber outlet 38 does not increase gradually and is instead suddenly released to its maximum width, because the sealing lip of the valve body 37 can no longer engage on the inner circumference of the valve chamber 36.

It is claimed:

1. A portable dispenser for discharging media including flowable media in at least one dose quantity, said dispenser being enclosable in a person's hand and being operationally free of external supply lines, said dispenser comprising:

a dispenser base;

manually operable actuating means for actuating discharge of the media while simultaneously carrying said dispenser in the hand, said actuating means including a handle unit manually displaceable with respect to said dispenser base over an actuating path for actuating the discharge, the handle unit including at least one handle;

a medium outlet for expelling the media out of said dispenser; and, a media duct issuing into said media outlet;

distributing means disposed upstream of said media outlet, said distributing means including a media receiver and a receiver face for finely depositing and distributing the dose quantity in a distributing state, in which the dose quantity is distributed in an adhering coating on said media receiver;

conveyor means for expelling substantially only said dose quantity away from said media receiver, said conveyor means including a pressurizing member for pressurizing the media while in said media receiver; and, said dispenser base including a discharge head displaceable with respect to a base component over said actuating path, said discharge head being provided with said media outlet.

2. The dispenser according to claim 1, wherein said conveyor means is provided for expelling the dose quantity substantially entirely in a single expelling pulse, said media receiver (10, 10a) being provided for spreading the dose quantity over an area and forming a micro pattern upon action of a surface tension of said media, said media receiver having conical circumferential faces directly interconnected to provide guide faces for guiding the media toward the media outlet.

3. The dispenser according to claim 1, wherein after expelling substantially only the dose quantity away from said media receiver, said media receiver is refillable with a next dose quantity by manually actuating said handle unit over said actuating path, said media receiver being entirely encapsulated inside said dispenser base.

4. The dispenser according to claim 1, comprising a feed duct for feeding said media receiver with the dose quantity and thereby apply a media coating on said receiver face, said feed duct and said conveyor means separately connecting to said media receiver, said conveyor means being provided for feeding a conveyor flow through said media receiver to thereby unbind the media from said media receiver and entrain the media with the conveyor flow out of said media outlet, said conveyor means including a manually operable conveyor pump.

5. The dispenser according to claim 1, wherein:

said media receiver comprises a filling body and an outermost receiver boundary separate from and narrowly enveloping said filling body for substantially uniformly distributing the media over a distributing space including microporous distribution in a micro pattern; and, within an outermost receiver boundary said medium receiver including finely fragmented surface structure for simultaneously adhesively binding the quantity dose after wetting by the media, said filling body resiliently connecting to said outermost receiver boundary.

6. The dispenser according to claim 1, wherein said media receiver comprises receiver members including at least one receiver body and an outermost circumferential boundary enveloping said receiver body, one of said receiver members being radially resiliently deformable.

7. The dispenser according to claim 1, wherein:

said media receiver comprises at least one of cross linked fiber membrane structure, resiliently compressible sponge structure, precompressed porous structure, a plurality of pore chambers of varying chamber width extensions and chamber configurations, and compressed under pretension, a foam structure; and, a receiver body defining an outermost body boundary, within said outermost body boundary said receiver body being substantially entirely uniformly filled with body material and receiver cavities, said body material and said receiver cavities directly connecting to said outermost body boundary, under resilient pre-tension.

8. The dispenser according to claim 1, wherein said media receiver defines an axial extension and a spatial center, a feed duct being provided for depositing the quantity dose inside a distributing space of said media receiver as a film, said feed duct directly connecting to said media receiver transverse to said axial extension and substantially directed towards said spatial center, said media receiver being assembled from directly interconnected receiver members including a filling body and a receiver boundary enveloping said filling body, one of said receiver members being inherently resilient and resiliently moveable under flow stresses of the media for releasing the media from said distributing space.

9. The dispenser according to claim 1, wherein said conveyor means (11, 11*a*) directly and substantially equiaxially connects to said media receiver (10, 10*a*) through an orifice where said media receiver has a substantially smallest cross-section of a varying cross-sectional extension, said media receiver including a peripheral circumference and a media exit connecting only to a minor section of said peripheral circumference, said media receiver entirely covering said orifice.

10. The dispenser according to claim 1, wherein said conveyor means (11, 11*a*) including a manually pressurizable pressure chamber (54) and an outlet valve (35) connecting said pressure chamber (54) with said media receiver (10) is provided for creating a shock wave of a gas and for feeding said shock wave directly to the dose quantity stationarily deposited at said media receiver prior to creating said shock wave.

11. The dispenser according to claim 1, wherein said conveyor means are provided for expelling the media at said medium outlet as an un-atomized drop.

12. The dispenser according to claim 1, wherein said conveyor means are provided for conveying residues of the media under pressure out of said medium outlet when finishing expelling the dose quantity.

13. The dispenser according to claim 1, wherein said media receiver defines a maximum volumetric quantity fillable with the media, the dose quantity filling said media receiver for being expelled being smaller than said maximum volumetric quantity.

14. The dispenser according to claim 1, wherein said receiver face includes a smooth surface, said media receiver including receiver members including a filling unit and a receiver boundary substantially coaxial with said filling unit and said medium outlet, one of said receiver members including at least one conical guide face for guiding the media toward said medium outlet.

15. The dispenser according to claim 14, wherein said receiver boundary and said filling unit include conical sections.

16. The dispenser according to claim 1, wherein said handle and said conveyor means are operable away from first and second initial states, a first return spring being included for returning said handle to said first initial state when actuated and a second return spring being included for returning said conveyor means to said second initial state, said second return spring being coaxial with said conveyor means.

17. The dispenser according to claim 1, further comprising:

a thrust piston pump operable with said handle for filling said media receiver with the dose quantity under media pressure, said thrust piston pump including a pump chamber and an outlet valve for passing the media from said pump chamber to said media receiver, said outlet valve being opened when said actuating path reaches a given point; and, a return spring for reclosing said outlet valve and for simultaneously returning said thrust piston pump to an initial unactuated rest position, said thrust piston pump defining a preassembled unit to be connected to a media container supplying said pump chamber with the dose quantity when actuating said handle.

18. The dispenser according to claim 17, wherein:

said thrust piston pump and a pump casing form a piston unit;

said media container is volumetrically variable and includes a container boundary operably displaceable with respect to said pump casing, said pump casing freely extending inside said media container; and, said outlet valve including a valve body commonly displaceable with said piston unit, relative to said pump casing.

19. The dispenser according to claim 1, wherein said actuating means are provided for pretensioning said conveyor means by generating a conveying tension and for thereafter refilling said media receiver.

20. A dispenser for discharaing media including flowable media in at least one dose quantity, comprising:

a dispenser base, manually operable actuating means movable relative to said dispenser base for discharging the media, a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver, said media receiver defining a general flow direction when said media is expelled; and, said media receiver having a cross-section transverse to said flow direction, said cross-section at least one of increasing and decreasing in said flow direction.

21. The dispenser according to claim 20, further comprising a media feed inlet connecting directly to said media receiver, said cross-section of said media receiver increasing substantially continuously in a direction away from said feed inlet.

22. A dispenser for discharging media including flowable media in at least one dose quanity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

said media receiver having a cleft receiver body with outermost and innermost body surfaces and defining body cross-sections, said body cross-sections including hollow cross-sections externally bounded by said outermost body surface and internally bounded by said innermost body surface; and, conveyor means for expelling substantially only said dose quantity away from said media receiver.

23. A dispenser for discharging media including flowable media in at least one dose quantity, comprising:

a dispenser base:

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

a pressure outlet through which said conveyor means issues directly into said media receiver; and, on a side remote from said pressure outlet, said media receiver having a depression bounded by a guide face for transversely guiding the media out of said media receiver and towards said media outlet.

24. A dispenser for discharging media including flowable media in at least one dose quantity, comprising;

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

at least one impact atomizer, disposed downstream of said media receiver and upstream of said media outlet, at least one impact atomizer for additionally atomizing the media delivered to send impact atomizer in a pre-atomized flow; and, a deflection duct directly connecting said media receiver with said impact atomizer.

25. The dispenser according to claim 24 said media outlet provides a last contact of the media with said dispenser, said media outlet having a linear final nozzle duct with an upstream duct end and a nozzle opening at a downstream duct end, said impact atomizer including an impact surface directly opposing said upstream duct end of said final nozzle duct.

26. A dispenser for discharging media including flowable media in at least one dose quantity comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

a nozzle body, said media outlet traversing said nozzle body; and, said media receiver and said nozzle body commonly providing a nozzle unit for mounting on said dispenser base, said nozzle unit including a core body located inside said nozzle body and directly connecting to said media receiver.

27. A dispenser for discharging media including flowable media in at least one dose quantity comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

a media pump for feeding the media directly to said media receiver; and, said conveyor means including a conveyor pump for feeding a conveying fluid to said media receiver, entraining the media deposited at said media receiver and carrying the dose quantity away from said media receiver in a single conveying pulse.

28. A dispenser for discharging media including flowable media in at least one dose quantity comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

said conveyor means including a conveyor pump operable with said actuating means, an energy capacity being provided for positively driving said conveyor pump over a pump stroke; and, control means for releasing said energy capacity so as to create a fluid shock wave for expelling the dose quantity intermediately stored within said media receiver away from said media receiver.

29. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

control means for positively controlling a discharge cycle including discharging the media out of said media outlet, said control means being provided for depositing the dose quantity at said media receiver prior to at least one of expelling a conveying fluid into said media receiver, pressurizing the conveying fluid up to an initial conveying pressure, and manually transferring said dispenser to a locked trigger state, said trigger state being manually releasable to actuate discharge of the dose quantity, after depositing the dose quantity and until discharge of the media out of said media outlet is completed, discharge of the media to said media receiver being prevented.

30. A dispenser for discharging media including flowable media in at least one dose quantity, comprising:

a dispenser base;

manually operable actuating means movable relative to said dispenser base for discharging the media, said actuating means including first and second actuating units reciprocally rotationally displaceable and a pitch gear, said pitch gear being driveable by manually displacing said second actuating unit with respect to said first actuating unit over a control motion defining a control stroke;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver; and, conveyor means for expelling substantially only said dose quantity away from said media receiver.

31. The dispenser according to claim 30, wherein said control motion is provided for simultaneously at least one of preparing said dispenser for subsequently triggering discharge of the dose quantity, filling said media receiver with the dose quantity, compressing a fluid quantity stored in said conveyor means, and freeing said media outlet from a closure cover.

32. A dispenser for discharging media including flowable media in at least one dose quantity comprising:

a dispenser base;

manually operable actuating means movable relative to said dispenser base for discharging the media;

a medium outlet for expelling the media out of said dispenser;

a media duct issuing into said media outlet:

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

said actuating means including a trigger handle for manually triggering said conveyor means; and, a gripping handle for manually holding said dispenser, said trigger handle being at least partly countersunk within said gripping handle.

33. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver; and conveyor means for expelling substantially only said dose quantity away from said media receiver, said conveyor means including an outlet valve having a valve chamber, said valve-chamber directly issuing into said media receiver.

34. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver; and, first and second separate discharge units, at least one of said discharge units including a media container and an actuating stem, said first and second discharge units being reciprocally separable without destructive disassembly.

35. The dispenser according to claim 34, wherein:

said second discharge unit includes said media container and a thrust piston pump for repeatedly depositing the media at said media receiver; and, said first discharge unit includes a discharge head, said discharge head providing a coupling member for detachably receiving said actuating stem in a substantially linear coupling motion.

36. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver, a first pressure chamber for depositing the dose quantity at said media receiver;

said conveyor means including a second pressure chamber; and, a discharge head including said media outlet and being located between said first and second pressure chambers.

37. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

said conveyor means including a first discharge unit for discharging pressurized gas;

a second discharge unit for delivering the dose quantity to said media receiver; and, said dispenser having an outermost casing, both said first and second discharge units being located substantially entirely inside.

38. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

said dispenser defining an overall longitudinal extension and an outermost outside, a casing extending over said longitudinal extension and having an outermost surface defining said outermost outside;

a discharge head separate from said casing, said media outlet being provided in said discharge head; and, said discharge head being substantially entirely located within said casing when said media is discharged out of said media outlet.

39. A dispenser for discharging media including flowable media in at least one dose quantity, comprising:

a dispenser base;

manually operable actuating means movable relative to said dispenser base for discharging the media;

a medium outlet for expelling the media out of said dispenser;

a media duct issuing into said media outlet;

upstream of said media outlet distributing means disposed upstream of said media outlet and including a media receiver, the media receiver being provided for finely depositing and distributing the dose quantity in a distributing state, in which the dose quantity rests in a substantially distributed and adhering micro pattern on said media receiver;

conveyor means for expelling substantially only said dose quantity away from said media receiver;

first and second separate discharge units, said second discharge unit including a media container;

said dispenser including an outermost casing, said outermost casing having a service opening for inserting and removing said second discharge unit;

a closure for closing said service opening; and, said casing providing a handle for operating said conveyor means.

40. A portable dispenser for discharging media including flowable media in at least one dose quantity, said dispenser being enclosable in a person's hand and including a media container for storing the media to be discharged, said dispenser comprising:

a dispenser casing;

manually operable actuating means for actuating discharge of the media while simultaneously carrying said dispenser in the hand, said actuating means including a handle manually displaceable with respect to said dispenser casing over an actuating path for actuating the discharge;

a medium outlet for expelling the media out of said dispenser;

a discharge unit, including a media pump and said media container, for repeatedly and individually supplying said media pump with the dose quantity upon actuating said media pump with said handle over a pump stroke, said media pump including a pump casing and a stroke unit operationally axially unidirectionally displaceable with respect to said pump casing with said handle from an initial state over said pump stroke up to a stroke end; and, a unit sleeve circumferentially enveloping said discharge unit and preassembled with said discharge unit by axially inserting said discharge unit inside said unit sleeve, upon unidirectionally actuating said handle firstly said media pump being axially actuated over said pump stroke without displacing said unit sleeve with respect to said pump casing, whereafter said unit sleeve is axially displaced with respect to said dispenser casing commonly with said pump casing and said media container over a control path; and, control means operated with said handle, said control means controlling said unit sleeve to begin moving over said control path when said stroke end is reached.

41. The dispenser according to claim 40, wherein said pump casing is rigidly connected to said media container with a fixing sleeve separate from and enveloping said pump casing, said fixing sleeve directly connecting to a sleeve extension extending toward said media outlet, said media pump being a thrust piston pump and said stroke unit including a piston unit including a piston shaft, said piston shaft traversing said sleeve extension downstream and being axially traversed by an outlet duct supplying the dose quantity out of said media pump to said media outlet, an end duct being provided and including an upstream end and a downstream end defining said medium outlet, an intermediate duct directly connecting downstream to said end duct, said intermediate duct being bounded by and between bounding members including a core unit and a nozzle member narrowly enveloping and circumferentially rigidly connected to said core unit, said nozzle member and said piston shaft rigidly directly connecting to a nozzle holder made in one part and operationally displaceable with respect to said pump casing and said dispenser casing over said pump stroke while said unit sleeve remains stationary with respect to said dispenser casing, a snap connection being included and connecting said nozzle member and said piston shaft to said nozzle holder, within said nozzle member said intermediate duct including a duct section oriented transverse to said end duct and directly connecting to said upstream end.

42. The dispenser according to claim 41, wherein said nozzle member is a nozzle cap including a cap end wall bounding said end duct in one part, said core unit directly opposing said upstream end and being coaxial with said upstream end, said intermediate duct being commonly bounded by opposing circumferential faces of said nozzle cap and said core unit.

43. The dispenser according to claim 41, wherein said intermediate duct and said end duct are circumferentially enveloped by said nozzle holder substantially up to said media outlet, upstream of said media outlet a cleft receiver being provided for finely depositing and distributing the dose quantity in a distributing state, conveyor means and resilient structure being included for expelling substantially only the dose quantity away from said media receiver and said dispenser.

44. The dispenser according to claim 40, wherein said dispenser casing is located outermost of said dispenser to provide a holding grip for manually holding said dispenser, said unit sleeve being axially inserted inside said dispenser casing, said control means including a control sleeve operationally displaceable by actuating said handle and coaxial with said unit sleeve, said control sleeve operationally extending inside said dispenser casing and directly engaging said dispenser casing at an inner casing circumference.

45. The dispenser according to claim 44, further comprising:

said handle including a handle cap directly connecting to and closing said dispenser casing at an open casing end, said handle cap being coaxial with said dispenser casing and including a cap end wall partly freely exposed, a projection extending from inside said cap end wall and directly connecting to said control sleeve;

an axial snap connection directly connecting said handle cap with said dispenser casing against axial withdrawal of said handle cap;

a restoring spring for returning said medium pump to said initial state; and, means for operationally axially resiliently tensioning said unit sleeve with respect to said dispenser casing.

46. A dispenser for discharging media including flowable media in at least one dose quantity, comprising:

a dispenser base;

manually operable actuating means including a discharge head displaceable with respect to a base component over an actuating stroke and having a media outlet for expelling said media out of said dispenser;

a media duct issuing into said media outlet;

distributing means disposed upstream of said media outlet and including a media receiver entirely encapsulated inside said dispenser base, the media receiver being provided for finely depositing and distributing the dose quantity in a distributing state, in which the dose quantity rests in a substantially distributed and adhering micro pattern on said media receiver; and, conveyor means for expelling substantially only said dose quantity away from said media receiver.

* * * * *